United States Patent [19]

Valenty

[11] Patent Number: 5,456,905
[45] Date of Patent: * Oct. 10, 1995

[54] QUICK-DRYING NAIL COATING METHOD AND COMPOSITION

[75] Inventor: Vivian B. Valenty, Tempe, Ariz.

[73] Assignee: Ultraset Limited Partnership, Scottsdale, Ariz.

[*] Notice: The portion of the term of this patent subsequent to Jun. 2, 2009 has been disclaimed.

[21] Appl. No.: 964,953

[22] Filed: Oct. 22, 1992

Related U.S. Application Data

[63] Continuation-in-part of Ser. No. 852,319, Mar. 18, 1992, which is a continuation-in-part of Ser. No. 535,596, Jun. 11, 1990, Pat. No. 5,118,495, which is a continuation-in-part of Ser. No. 394,200, Aug. 15, 1989, Pat. No. 5,130,551, and Ser. No. 235,349, Aug. 23, 1988, abandoned.

[51] Int. Cl.⁶ ................. A61K 7/043; C09D 101/08; C09D 133/10; C08L 1/18
[52] U.S. Cl. .................. 424/61; 427/508; 524/35; 524/560; 522/44; 522/72; 522/89
[58] Field of Search .............. 424/61; 427/54.1, 427/53.1; 524/35, 560; 522/44, 89

[56] References Cited

U.S. PATENT DOCUMENTS

| | | | |
|---|---|---|---|
| 2,262,274 | 11/1941 | Fingerlin | 34/202 |
| 2,374,472 | 4/1945 | Corbett | 34/202 |
| 3,749,592 | 7/1973 | Gaske et al. | 522/89 |
| 3,844,790 | 10/1974 | Chang et al. | 430/281 |
| 3,896,014 | 7/1975 | Rosenberg | 204/159.23 |
| 3,928,113 | 12/1975 | Rosenberg | 156/344 |
| 4,066,582 | 1/1978 | Babian et al. | 524/31 |
| 4,126,675 | 11/1978 | Boulogne et al. | 424/61 |
| 4,596,260 | 6/1986 | Giuliano | 132/73 |
| 4,855,212 | 8/1989 | Targ et al. | 522/89 |
| 5,118,495 | 6/1992 | Nafziger et al. | 424/61 |

*Primary Examiner*—Edward J. Webman
*Attorney, Agent, or Firm*—Antonio R. Durando; Harry M. Weiss

[57] ABSTRACT

A photo-reactive nail polish coating composition that cures quickly upon exposure to natural light. The coating consists of a polymer formed from a composition comprising nitrocellulose, a photo-reactive monomer, a photoinitiator and a reaction inhibitor, resulting in a product compatible with commercially available nail polish of any color and removable by standard acetone-based polish removers. It is also compatible with every-day chores because it is insoluble in water. The composition is not phototoxic and has very low potential for skin irritation or sensitization. The photo-reactive coating is applied over the wet nail polish and then exposed to light, causing the nail polish to dry in a few minutes.

21 Claims, No Drawings

QUICK-DRYING NAIL COATING METHOD AND COMPOSITION

RELATED APPLICATIONS

This application is a continuation-in-part of U.S. application Ser. No. 07/852,319, filed Mar. 18, 1992, which is a continuation-in-part of U.S. application Ser. No. 07/535,596, filed Jun. 11, 1990, and issued as U.S. Pat. No. 5,118,495 on Jun. 2, 1992, which was filed as a continuation-in-part of U.S. application Ser. No. 07/394,200, filed Aug. 15, 1989, and issued as U.S. Pat. No. 5,130,551, on Jul. 14, 1992, and of U.S. application Ser. No. 07/235,349, filed Aug. 23, 1988, abandoned. The sole inventor of the present application is also the sole inventor of Ser. No. 07/852,319, and a joint inventor of Ser. No. 07/535,596, whose other joint inventors were also joint inventors of Ser. No. 07/394,200, and Ser. No. 07/235,349.

BACKGROUND OF THE INVENTION

1. Field of the Invention

This invention pertains to the general field of rapidly drying coatings for lacquers and enamels applied to human nails. In particular, the invention concerns a new composition and method for its application which provide a smooth, hard and glossy coating that cures in minutes and is easily removable by commercial nail polish removers.

2. Background of the Invention

Nail polish, lacquers and enamels comprise a class of products regularly used by modern women as part of their beauty care regimen. Enamels are available in a multitude of colors and it is not uncommon for women to strip and reapply nail enamels several times a week in order to match their wardrobe and makeup. This process is time consuming because three to four different layers of coating must be applied and allowed to air dry. Typically, a first layer of colorless base coat is applied, then two layers of color enamel and, finally, a layer of colorless enamel for gloss and protection. During the drying period, which can take as long as several hours, women have to refrain from tasks that might cause them to mar this painstakingly, and sometimes expensively, applied nail polish. Simple operations, such as opening a car door or extracting keys from a purse, can quickly ruin freshly applied fingernail enamel. Thus, in effect, they are prevented from using their hands in any normal everyday activity while the polish is drying. This is especially burdensome for beauty salon customers who need to be able to function normally immediately after receiving a manicure.

Realizing the burden that air drying methods put on people with freshly manicured hands, devices have been developed to try and expedite the drying process. See, for example, U.S. Pat. No. 2,262,274 to Fingerlin (1941) and U.S. Pat. No. 2,374,472 to Corbett (1945). These devices consist generally of a box-like dryer that blows or circulates hot or cold air on the nail's surface for a specified period of time. However, these devices can only dry the surface of the top coating on the nail and do not cause any drying underneath. Consequently, additional exposure to air is required to dry the lower coats of nail polish and in the meantime a manicure can be easily ruined if the nail's surface comes into contact with any hard surface. As a result, nail polish wearers still have to use their hands cautiously for several hours after application in order not to ruin the product of a manicure.

U.S. Pat. No. 3,896,014 and U.S. Pat. No. 3,928,113 to Rosenberg (1975) disclose a process for coating nails comprising the steps of applying a water soluble base coat to the nails, allowing the base coat to dry, then applying a photocurable nail lacquer and curing the lacquer by exposing it to sufficient amounts of radiation. The inventive purpose behind this patent was to try to develop a nail coating that could be removed by water instead of an acetone based commercially available nail polish remover. Accordingly, the nail lacquer was specifically designed for a water soluble base coat, and commercially available nail polishes could not be used in the process. The water soluble base coat that rendered the photocured composition strippable also made the cured film incompatible with daily human functions such as hand and dish washing, bathing, and all other activities involving the immersion of nails in water.

U.S. Pat. No. 4,596,260 to Giuliano (1986) discloses a process of applying a photocurable coating to an artificial nail tip whereby upon exposure to suitable radiation the coating hardens to give the appearance of a natural nail. As it consists of a polyfunctional polymer to which the monomer is crosslinkable, the photocurable coating is very difficult to remove if applied on top of commonly used nail polishes.

Finally, in U.S. Pat. No. 4,126,675 (1978), Boulogne et al. teach a nail polish composition including a copolymer resin based on a mixture of methyl methacrylate and hexyl methacrylate. These two substances are mixed separately and caused to polymerize to form a copolymer under specific conditions before they are added to the balance of the ingredients comprising the nail polish. No polymerization occurs after the copolymer resin is mixed with the balance of the ingredients or after the resulting nail polish is applied on the nails of a user.

Thus, while these references are relevant to show the general state of the art, they are not directed to the inventive purpose behind the subject invention, which is to rapidly dry a protective coat that can be applied on any commercially available nail polish, lacquer and enamel. Several commercial products have already been introduced that promise a reduction of the drying time of nail coatings. These products include silicone and mineral oils, which provide a slippery surface to the enamel and thus render it non-tacky; but they leave the solvents in place and do not harden the enamel. Also employed are cyclic siloxanes and other low boiling liquids that dry the top surface of the enamel as they evaporate with some of the solvents near the surface. The problem here is that the bulk of the multilayer enamel coating is left laden with solvent and still takes hours to dry and harden.

Infrared lamps, which aid the volatilization of the solvents in the enamel by increasing its temperature, reduce the drying time to about 30 minutes. This is still unsatisfactory, though, for today's growing number of working women who have to juggle their time between a job and housework. Thus, a method that will further reduce the drying time of multilayer enamel coatings is still needed and it could be expected to have great commercial value in the cosmetics industry.

The compositions disclosed in my copending application Ser. No. 07/052,319 and in U.S. Pat. No. 5,118,495 amount to a great improvement toward the solution of the problems mentioned above. Those compositions are described in combination with the use of artificial ultraviolet light to form a polymeric top coat within minutes of application over an enamel layer. The new matter of this continuation-in-part application is based on the discovery that the same compositions may be utilized with comparable results even in the absence of artificial ultraviolet radiation.

SUMMARY OF THE INVENTION

An object of the present invention is to provide a photoreactive nail coating composition containing monomer substances that polymerize in a matter of minutes.

Another object of the invention is to provide a photopolymerizable nail coating composition that dries over multiple coats of nail enamels within a few minutes of exposure to light.

A further object is to provide a photo-polymerizable composition that is compatible with the majority of commercially available nail polishes, lacquers and enamels.

Another goal of the invention is a photo-polymerizable composition that is essentially odorless and colorless after application.

Yet another object is to provide a photo-polymerizable composition that is not phototoxic and that produces very low skin irritation.

Finally, a goal of the invention is to provide a photo-polymerizable composition that after curing is still easily removable by means of commercially available nail polish removers.

Presently, in beauty salons and homes around the world, nail polish is applied in a three step process. First, a base-coat is used to fill ridges in the nail and to prevent the colored polish or enamel, applied in step two, from staining the natural nail. Second, two coats of colored polish or enamel are applied. Two coats are usually used in order to provide an opaque and colorful finish. Third, a clear top coat of lacquer is applied to protect the lower layers, applied in step two, to give the nail a prominent shine and to provide extended wear.

The present invention provides a coating for nails that is applied as the top coat in step three. Like present-day top coats, this coating is clear, it imparts a prominent shine, and also provides extended wear. Unlike present-day top coats, the coating is photo-reactive. Thus, after this coating has been applied as a top coat, the present invention may use a source of ultraviolet radiation, in safe dosages, to irradiate the nail and cause the top coat to react, resulting in the nail polish or enamel underneath drying within a few minutes. The required apparatus is described in copending application Ser. No. 394,200, U.S. Pat. No. 5,130,551. Alternatively, the top coat of the present invention may be allowed to dry under exposure to natural light, in which case it takes approximately twice as long to dry.

The photocuring of the top coat renders the multilayer enamel system dry to the touch immediately after exposure to ultraviolet light, as described in the copending applications. The coat is readily resistant to marring by actions such as rubbing with fingertips and hitting by blunt objects. After 5–15 minutes, it is essentially rock-hard, as demonstrated by its resistance to marring when scraped with fingernails. If, instead, the top coat is not exposed to an ultraviolet light, it is found that it still readily becomes resistant to marring, but it takes 10–30 minutes before it is completely cured.

These and other objects, features and advantages of the present invention, as well as details of the preferred embodiment thereof, will be more fully understood from the following detailed description.

DETAILED DESCRIPTION OF THE PREFERRED EMBODIMENT

Nail enamels are generally composed of resins, pigments, dyes, plasticizers, and solvents. Mixtures of low and medium boiling solvents are used to control the rate of evaporation. A high boiling solvent slows the drying process but produces a glossier film; therefore, the drying time of an enamel depends to a large extent on the solvent system. It is easily obvious to a person skilled in the art that one can speed up the enamel's drying time by substituting polymerizable liquid monomers for the solvent system (i.e., the liquid monomers act as the solvent system for the solid components of the enamel). The enamel is then dried and hardened by polymerization of the liquid monomers using a catalytic system that is triggered by heat or light.

Such a method of nail coating, formulated into enamels with a variety of dyes and pigments, constitutes a new family of nail enamels that could make current products obsolete. The problem with such systems is that the coatings are difficult to remove. U.S. Pat. No. 3,928,113, described above, offered a solution by the use of a water soluble base coat before applying the photocurable nail enamel. As opposed to that method, the coating of this invention is resistant to the usual tasks of dish washing, hand washing, or other chores involving the contact of fingers with hot water.

Furthermore, this prior art is different from the present invention in composition, as well as in function or use. U.S. Pat. No. 3,928,113 claims a method of coating human nails whereby a water soluble or swellable base coat is first applied, followed by a photocurable pigmented or unpigmented polymer composition to provide a multilayer nail enamel that is removable when soaked in hot water. The present invention does not utilize a water soluble or swellable basecoat because, as explained above, that approach is not compatible with normal every day tasks that involve soaking the hands in warm or hot water. In addition, the photocurable composition of this prior art also serves as the principal enamel and therefore is pigmented in most cases. The present invention is clear and unpigmented for use as a topcoat on any commercially available nail enamel. Finally, from a compositional point of view, this prior art discloses a polythiol as an essential ingredient in the claimed composition. The present invention does not require a polythiol.

U.S. Pat. 4,596,260 utilizes known photopolymerizable compositions for adhering preformed artificial nail tips to natural nails. This composition also differs from the present invention not only in function, but in formulation as well. That patent claims a composition wherein a monomer is crosslinkable with the required polymer component which is claimed to be a low molecular weight acrylated urethane oligomer free of reactive isocyanate groups. Such a reactive polymer is not required in the present invention.

Furthermore, that patent describes in detail the ultraviolet lamp which is suitable for photocuring according to the claimed method. Although no specification on the lamp intensity is provided, an example is given with a lamp having 100 watt capacity. The present invention may utilize a lamp that is of low intensity (i.e., less than 10 watts) or, as specified herein, no lamp at all (under natural light-on). As a result, even when a lamp is used, the radiation used in the present invention is safer and less annoying to the eyes, as described in U.S. Pat. No. 5,130,551 than that produced by the lamp described in U.S. Pat. No. 4,596,260.

In general, the prior art, which include both the patent literature and polymer texts, is rich with references to photocurable compositions. Typically, these compositions include at least one suitable polyfunctional polymer or oligomer, a photoinitiator and a liquid monomer in which the various other ingredients are soluble, the monomer being crosslinkable with the polyfunctional polymer in the presence of actinic radiation (e.g., ultraviolet radiation) to form a plastic film. As is understood in the art, the degree of firmness is in part dependent upon the degree of crosslinking and one skilled in the art understands that varying the ratio of monomer to polymer can provide greater or lesser firmness or rigidity of the product. Polyfunctional monomers are also used in prior art and the ratio of polyfunctional monomer to monofunctional monomer is varied as well to provide greater or lesser firmness or rigidity to the product. Moreover, the reactivity of the functionality itself affects the curing rate and also determines the firmness or rigidity of the product. For example, acrylates are more reactive and form harder coatings than the corresponding methacrylates.

On the bases of prior art knowledge, useable photoreactive compositions for use in conjunction with an ultraviolet rapid-dry device have been developed and are described in copending application Ser. No. 07/852,319 and in U.S. Pat. No. 5,118,495. As mentioned above, for example, it was found that acrylates react faster than methacrylates and result in harder photocured systems, but methacrylates have lower skin irritation and sensitization potential. Accordingly, compositions based on methacrylate functionality alone are preferable and have become the focus of ongoing research. In the course of further investigation, a further welcomed but unexpected observation was made that a totally methacrylate monomer system, in the presence of nitrocellulose, cures hard within three minutes of exposure to a low intensity, long wave ultraviolet lamp. Also surprisingly, it was found that a methacrylate system consisting of only monofunctional monomers, instead of the difunctional monomers taught by prior art, cured into a hard coat over three layers of nail enamel within three minutes of exposure to the prototype lamp. As expected, such systems have lower skin irritating properties than a similar system comprised of an acrylate monomer.

Accordingly, the photo-reactive coating of this invention is comprised of a primary film-forming resin in a wetting agent and in a solvent carrier, photocurable monomers (mono or difunctional), a photoinitiator and an inhibitor. As these ingredients are commonly found independently in nail coating products, one skilled in the art would readily understand the purpose for each in the photo-reactive coating. Similarly, the method of mixing and preparation of the resulting composition would be obvious in the art. Consequently, these ingredients and the process of preparation of the resulting product need not be discussed in great detail.

In the preferred embodiment of the coating, the primary film-forming resin (polymer) is nitrocellulose, which is available commercially in a wetting agent to reduce its reactivity and potential explosivity. The particular wetting agent used with nitrocellulose is not critical to the invention, so long as one is present to avoid danger of explosion. A wetting agent is an inherent requirement for being able to use nitrocellulose, which itself alone (i.e., not the wetting agent) is one of the active ingredients in the formulation of the invention. Thus, commercial nitrocellulose such as is sold, for instance, by the Aqualon Company of Wilmington, Del., and by the Wolff Walsroder AG company of Walsrode, Germany, is available in either ethyl, isopropyl, or n-butyl alcohol as wetting agent, according to customer specification. Any of these (or other) nitrocellulose wetting agents would enable one to practice the invention in equivalent fashion. It should be noted that the term wetting agent, as used in the context of nitrocellulose, is not synonymous with the term surfactant, as in the detergent industry. The two terms are distinct and wetting agent simply refers to a means for keeping the nitrocellulose in a wet state. Water is also a suitable wetting agent, but it is not used in the invention because it is incompatible with the other ingredients. On the other hand, the mentioned wetting agents are used not because they are surfactants (although they also lower the surface tension of water), but because they are miscible with the solvents of the invention.

The wet nitrocellulose is used in a carrier solvent, such as ethyl acetate or n-butyl acetate, so that it can be mixed with the other ingredients of the invention and stored as a homogeneous solution before use. These solvents (ethyl acetate and n-butyl acetate) are only two of many solvents that could be used as carriers for the wet nitrocellulose, all of which would be obvious to one skilled in the art. These include, for example, methyl acetate, ethyl acetate, n-propyl acetate, isopropyl acetate, n-butyl acetate, isobutyl acetate, sec-butyl acetate, ethyl propionate, acetone, methyl ethyl ketone, methyl n-propyl ketone, methyl isopropyl ketone, methyl n-butyl ketone, methyl isobutyl ketone, methyl secbutyl ketone, 2-ethyl-n-butyl acetate, and 2-ethoxy ethyl acetate. In addition, hydrocarbon solvents, such as pentanes, hexanes and heptanes, may be used in conjunction with the above listed esters and ketones. As in the case of wetting agents, the solvent is not part of the inventive step of the composition, but it is used only as a carrier for the nitrocellulose ingredient. The particular solvent used as carrier has no effect on the removability of the claimed coating, which depends instead only on the properties of the polymerized composition. It is found that the presence of these solvents also improves the coating's compatibility with commercially available colored nail enamels and lacquers.

Nitrocellulose is used in concentrations from 5 to 30 percent by weight (preferably from 17 to 23 percent) of the total composition. Correspondingly, as a result of the nitrocellulose/isopropanol ratio normally found in commercial products, isopropanol will be present in concentrations varying approximately from 2 to 13 percent by weight. The solvent, whether ethyl acetate or n-butyl acetate, is used in approximately 50 percent greater quantity than nitrocellulose. In any event, the compositions of all ingredients with solvent characteristics may be varied to obtain the desired viscosity of the final product.

Photoreactive monomers are used, either alone or in mixture, in total concentrations between 2 and 55 percent by weight. Optimal concentrations are from 5 to 43 percent by weight of the total composition. In general, it was found that dimethacrylate monomers of the following formula are acceptable for practicing this invention:

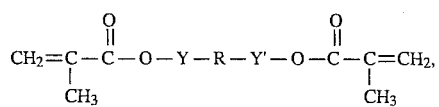

where Y and Y' may be the same or different but can be any hydrocarbyl difunctional radicals with 1–4 carbon atoms; R is any hydrocarbyl difunctional radical with 1–10 carbon atoms; and the Y and Y' radicals may be joined to the R radical by means of any organic group with two free bonds, known to those skilled in the art as linking radicals in which one or two atoms separate R from Y and Y', such as —O—, —NH—, —S—, —CO—, —CH$_2$—, —SO—, —SO$_2$—, —SO$_2$O—, —NH—CO—, and —NR'— where R' is an aliphatic monofunctional radical with 1–4 carbon atoms. R may be aliphatic, alicyclic or aromatic.

In particular, it was found that the following difunctional methacrylate monomers, together with monofunctional methacrylates according to the total quantities listed above, are particularly suitable in the percentages shown:

| Difunctional Methacrylate Monomer | Weight % Range | Optimal Range |
|---|---|---|
| 1,4 butanediol dimethacrylate | 0.4–10.0 | 0.5–5.5 |
| 1,3 butanediol dimethacrylate | 0.4–10.0 | 0.5–5.5 |
| diurethane dimethacrylate | 0.4–6.0 | 0.4–5.5 |

As mentioned above, though, and most significantly for the purposes of this invention, it was also found that monofunctional methacrylate monomers alone produce a rapidly curing product. Some of these methacrylate monomers and the corresponding ranges of use are given below:

| Monofunctional Methacrylate Monomer | Weight % Range | Optimal Range |
|---|---|---|
| ethyl methacrylate | 2.0–55.0 | 5.0–43.0 |
| cyclohexyl methacrylate | 2.0–55.0 | 2.0–20.0 |
| 2-ethylhexyl methacrylate | 2.0–55.0 | 2.0–20.0 |
| isobutyl methacrylate | 2.0–55.0 | 5.0–43.0 |
| n-butyl methacrylate | 2.0–55.0 | 5.0–43.0 |
| methyl methacrylate | 2.0–55.0 | 5.0–43.0 |
| isobornyl methacrylate | 2.0–25.0 | 2.0–6.0 |
| furfuryl methacrylate | 2.0–25.0 | 2.0–6.0 |
| tetrahydro furfuryl methacrylate | 2.0–25.0 | 2.0–6.0 |

The preferred monomers are methacrylic acid ester monomers, such as ethyl methacrylate or cyclohexyl methacrylate or, preferably, a mixture of the two within the total preferred concentrations listed above. In the place of cyclohexyl methacrylate, furfuryl- and tetrahydro furfuryl methacrylate have been found to result in a product with comparable curing characteristics. Similarly, isobutyl and methyl methacrylate can be used instead of ethyl methacrylate. Isobornyl methacrylate has been found to perform well in conjunction with diurethane dimethacrylate, with or without ethyl methacrylate. Since ethyl methacrylate acts as a solvent as well as a reactive monomer, its quantity must be adjusted as a function of the other monomers used to provide the desired product viscosity.

Any one of several known photoinitiators of the aryl or the alkyl aryl ketone type may be used to practice this invention. For example, these include photoinitiators such as benzophenone, diethoxyacetophenone, benzil diketal (BDK), as well as other well known products. It was found that 2-hydroxy-2-methyl-1-phenylpropanone, available, for example, as the product sold by EM Industries, Inc. under the trademark "Darocur 1173," is preferred. The photoinitiator is used in concentrations from 0.5 to 5 weight percent, preferably between 2 and 4 percent of the total composition.

Inhibitors to polymerization are a necessary ingredient of the claimed composition in order to provide shelf stability to the formulation. Useful inhibitors are also well known in the art and include hydroquinone and substituted analogs such as 4-methoxyphenol (MEHQ), either singularly or in combination with anti-oxidants to suppress yellowing. For example, MEHQ may be used at a concentration of about 25 to 200 ppm in combination with the anti-oxidant tris(4-t-butyl-3-hydroxy-2,6-dimethylbenzyl)-s-triazine-2,4,6-trione, sold as "Cyanox 1790" (a trademark of American Cyanamid Co.), at 0.25 weight percent of the total composition.

While the basic ingredients necessary to practice the invention are nitrocellulose, a photo-reactive monomer, a photoinitiator, and an inhibitor in quantities within the ranges described above, other ingredients may also be added to impart specific desirable characteristics. For example, surfactants like sorbitan trioleate may be added to improve homogeneity; plasticizers like dibutyl phthalate to flexibilize the cured coating; slip agents to give the material a lower coefficient of friction so that it may be applied more easily; and fragrances or masking agents to improve the product's odor.

The following examples list alternative formulations of the preferred embodiment of the coating according to this invention.

EXAMPLE 1

| Ingredient | Weight Percent |
|---|---|
| nitrocellulose | 19.5 |
| isopropanol | 8.4 |
| ethyl acetate | 27.9 |
| ethyl methacrylate | 26.7 |
| cyclohexyl methacrylate | 12.6 |
| 2-hydroxy-2-methyl-1-phenylpropanone | 4.0 |
| 4-methoxyphenol | 40 ppm |
| tris(4-t-butyl-3-hydroxy-2,6-dimethylbenzyl)-s-triazine-2,4,6-trione | 0.07 |
| sorbitan trioleate | 0.9 |

EXAMPLE 2

| Ingredient | Weight Percent |
|---|---|
| nitrocellulose | 18.3 |
| isopropanol | 7.9 |
| n-butyl acetate | 26.2 |
| ethyl methacrylate | 28.8 |
| cyclohexyl methacrylate | 13.6 |
| 2-hydroxy-2-methyl-1-phenylpropanone | 4.4 |
| 4-methoxyphenol | 42 ppm |
| tris(4-t-butyl-3-hydroxy-2,6-dimethylbenzyl)-s-triazine-2,4,6-trione | 0.02 |
| sorbitan trioleate | 1.0 |

EXAMPLE 3

| Ingredient | Weight Percent |
|---|---|
| nitrocellulose | 21.8 |
| isopropanol | 9.4 |
| ethyl acetate | 31.2 |
| ethyl methacrylate | 18.5 |
| cyclohexyl methacrylate | 14.4 |
| 2-hydroxy-2-methyl-1-phenylpropanone | 2.8 |
| 4-methoxyphenol | 114 ppm |
| tris(4-t-butyl-3-hydroxy-2,6-dimethylbenzyl)-s-triazine-2,4,6-trione | 0.26 |
| sorbitan trioleate | 1.0 |
| dibutyl phthalate | 0.4 |

-continued

| Ingredient | Weight Percent |
| --- | --- |
| fragrance | 0.2 |

EXAMPLE 4

| Ingredient | Weight Percent |
| --- | --- |
| nitrocellulose | 18.3 |
| isopropyl alcohol | 7.9 |
| hexane | 5.5 |
| ethyl acetate | 16.5 |
| ethyl methacrylate | 41.3 |
| 1,4 butanediol dimethacrylate | 2.75 |
| diurethane dimethacrylate | 2.75 |
| 4-methoxyphenol | 165 ppm |
| sorbitan trioleate | 0.83 |
| fragrance | 0.55 |
| 2-hydroxy-2-methyl-1-phenylpropanone | 2.75 |

EXAMPLE 5

| Ingredient | Weight Percent |
| --- | --- |
| nitrocellulose | 14.1 |
| isopropyl alcohol | 6.0 |
| ethyl acetate | 19.7 |
| ethyl methacrylate | 50.4 |
| 4-methoxyphenol | 129 ppm |
| 1,4 butanediol dimethacrylate | 2.5 |
| diurethane dimethacrylate | 2.6 |
| 2-hydroxy-2-methyl-1-phenylpropanone | 4.0 |

EXAMPLE 6

| Ingredient | Weight Percent |
| --- | --- |
| nitrocellulose | 18.0 |
| isopropyl alcohol | 7.7 |
| ethyl acetate | 58.3 |
| 1,4 butanediol dimethacrylate | 0.5 |
| diurethane dimethacrylate | 0.5 |
| ethyl methacrylate | 12.3 |
| 4-methoxyphenol | 148 ppm |
| 2-hydroxy-2-methyl-1-phenylpropanone | 2.0 |

EXAMPLE 7

| Ingredient | Weight Percent |
| --- | --- |
| nitrocellulose | 15.1 |
| isopropyl alcohol | 6.5 |
| diurethane dimethacrylate | 2.4 |
| 1,4 butanediol dimethacrylate | 3.96 |
| isobutyl methacrylate | 1.94 |
| isobornyl methacrylate | 4.31 |
| ethyl acetate | 62.5 |
| 4-methoxyphenol | 43 ppm |
| 2-hydroxy-2-methyl-1-phenylpropanone | 1.62 |

EXAMPLE 8

| Ingredient | Weight Percent |
| --- | --- |
| nitrocellulose | 20.0 |
| isopropyl alcohol | 8.6 |
| diurethane dimethacrylate | 2.9 |
| 1,4 butanediol dimethacrylate | 4.7 |
| isobornyl methacrylate | 2.3 |
| cyclohexyl methacrylate | 5.2 |
| ethyl acetate | 52.0 |
| 4-methoxyphenol | 26 ppm |
| 2-hydroxy-2-methyl-1-phenylpropanone | 3.1 |

EXAMPLE 9

| Ingredient | Weight Percent |
| --- | --- |
| nitrocellulose | 15.5 |
| isopropyl alcohol | 6.7 |
| diurethane dimethacrylate | 3.5 |
| 1,4 butanediol dimethacrylate | 5.1 |
| isobutyl methacrylate | 8.9 |
| ethyl acetate | 57.7 |
| 4-methoxyphenol | 22 ppm |
| 2-hydroxy-2-methyl-1-phenylpropanone | 1.7 |

EXAMPLE 10

| Ingredient | Weight Percent |
| --- | --- |
| nitrocellulose | 20.9 |
| isopropyl alcohol | 8.9 |
| diurethane dimethacrylate | 3.3 |
| 1,4 butanediol dimethacrylate | 5.4 |
| ethyl methacrylate | 8.6 |
| ethyl acetate | 50.7 |
| 2-hydroxy-2-methyl-1-phenylpropanone | 2.1 |

As seen from the examples above, the preferred photoreactive monomers are ethyl methacrylate and cyclohexyl methacrylate. These two monomers have very sharp and strong scents that are found to leave a residual odor in the finished manicure that may be objectionable to some people. In addition, the resulting compositions produce a film that is colorless immediately after curing but tends to become yellow after a few days of wear and exposure to sunlight, which is unacceptable for use in conjunction with light-colored polishes. Some commercial nail polishes are also found to react with these compositions to produce blue or purple discolorations.

When benzil diketal is used, the amount of photoinitiator needed for curing can be decreased to approximately 0.05 percent and still obtain complete polymerization by three-minute exposure to low power ultraviolet radiation of the kind emitted by the apparatus described in copending application Ser. No. 394,200, or by approximately five-minute exposure to natural light. As a result of the lower photoinitiator concentration, it is possible to also decrease the amount of inhibitor required for the desired shelf life. Finally, it was found that by combining the lower inhibitor concentration with a higher concentration of anti-oxidant, the resulting cured film did not tend to become yellow from exposure to sunlight and did not display blue or purple discolorations with commercial nail polishes. The amount of the inhibitor required with these lower photoinitiator concentrations is about 6 ppm if an anti-oxidant is present at concentrations greater than 0.1 percent (up to a maximum of about 1.00 percent) by weight of the total composition.

Moreover, it was found that the residual odor problem associated with the earlier preferred formulations (that is, those containing ethyl methacrylate and cyclohexyl methacrylate monomers) can be greatly corrected by reducing their concentration or by substituting all or part of them with butyl methacrylate monomers. The use of n-butyl methacrylate in concentrations between 6.48 and 7.14 percent by weight is preferred.

The formulations containing the reduced photoinitiator and inhibitor concentrations are still capable of polymerization within a few minutes, even if not exposed to an ultraviolet lamp. As in the prior formulations, the inhibitor in the reduced concentration is effective in keeping the uncured product stable for at least 18 months at 21° C. or for more than one week at 63° C. The stability at the latter temperature is necessary for the product to survive unrefrigerated transportation during the summer months.

The following examples define the composition of these improved formulations:

| Ingredient | Weight Percent |
| --- | --- |
| nitrocellulose | 21.3 |
| isopropyl alcohol | 9.1 |
| ethyl acetate | 50.2 |
| isobutyl acetate | 4.2 |
| ethyl methacrylate | 11.3 |
| cyclohexyl methacrylate | 1.4 |
| tris(4-t-butyl-3-hydroxy-2, 6-dimethylbenzyl)-s-triazine-2, 4,6-trione | 0.28 |
| benzil diketal | 0.17 |
| 4-methoxyphenol | 12 ppm |
| dibutyl phthalate | 0.57 |
| sorbitan trioleate | 1.13 |
| fragrance | 0.28 |

EXAMPLE 12

| Ingredient | Weight Percent |
| --- | --- |
| nitrocellulose | 22.9 |
| isopropyl alcohol | 9.8 |
| ethyl acetate | 32.75 |
| isobutyl acetate | 21.0 |
| n-butyl methacrylate | 7.14 |
| cyclohexyl methacrylate | 3.8 |
| tris(4-t-butyl-3-hydroxy-2, 6-dimethylbenzyl)-s-triazine-2, 4,6-trione | 0.42 |
| benzil diketal | 0.29 |
| 4-methoxyphenol | 11 ppm |
| dibutyl phthalate | 0.42 |
| sorbitan trioleate | 1.26 |
| fragrance | 0.21 |

In an effort to further improve the coloring of the coating of the invention, which is affected by the yellow nature of nitrocellulose, partial substitutes have been used that result in a lighter and longer lasting clear coating. These include cellulose acetate derivatives, such as cellulose acetate butyrate and cellulose acetate propionate, used in partial replacement of nitrocellulose. Examples of such formulations are given below. In addition, acrylate and/or methacrylate resins (both as polymers and copolymers) are also used as hardeners of the overall formulation. Note Examples 13 and 14, which include butyl methacrylate resin to add stiffness and hardness to the hardened coating.

EXAMPLE 13

| Ingredient | Weight Percent |
| --- | --- |
| nitrocellulose | 17.2 |
| isopropyl alcohol | 7.4 |
| ethyl acetate | 32.5 |
| isobutyl acetate | 30.0 |
| cellulose acetate butyrate | 2.47 |
| butyl methacrylate resin | 0.91 |
| n-butyl methacrylate | 6.48 |
| cyclohexyl methacrylate | 2.14 |
| tris(4-t-butyl-3-hydroxy-2, 6-dimethylbenzyl)-s-triazine-2, 4,6-trione | 0.10 |
| benzil diketal | 0.28 |
| 4-methoxyphenol | 9 ppm |
| sorbitan trioleate | 0.54 |

EXAMPLE 14

| Ingredient | Weight Percent |
| --- | --- |
| nitrocellulose | 9.3 |
| isopropyl alcohol | 4.0 |
| ethyl acetate | 53.2 |
| isobutyl acetate | 13.3 |
| butyl methacrylate resin | 0.73 |
| cellulose acetate propionate | 8.12 |
| n-butyl methacrylate | 6.65 |
| cyclohexyl methacrylate | 2.66 |
| tris(4-t-butyl-3-hydroxy-2, 6-dimethylbenzyl)-s-triazine-2, 4,6-trione | 0.27 |
| benzil diketal | 0.21 |
| 4-methoxyphenol | 9 ppm |
| dibutyl phthalate | 0.33 |
| sorbitan trioleate | 1.00 |
| fragrance | 0.22 |

EXAMPLE 15

| Ingredient | Weight Percent |
| --- | --- |
| nitrocellulose | 23.2 |
| isopropyl alcohol | 9.9 |
| ethyl acetate | 45.9 |
| isobutyl acetate | 12.74 |
| n-butyl methacrylate | 2.97 |
| cyclohexyl methacrylate | 2.97 |
| tris(4-t-butyl-3-hydroxy-2, 6-dimethylbenzyl)-s-triazine-2, 4,6-trione | 0.34 |
| benzil diketal | 0.31 |
| 4-methoxyphenol | 6 ppm |
| dibutyl phthalate | 0.42 |
| sorbitan trioleate | 1.27 |

It is also to be noted that acrylates and diacrylates may be used, either alone or in combination, as substitutes for the methacrylate and dimethacrylate monomers specified herein, as disclosed in the copending U.S. application Ser. No. 07/235,349 referenced above, filed Aug. 23, 1988, now abandoned. Because monomers of the acrylate and diacrylate families react more efficiently than methacrylates and dimethacrylates, they should be used in smaller concentrations in order to avoid an overly stiff and hard-to-remove coating. Thus, for example, while a formulation containing 55 percent by weight methacrylate and/or dimethacrylate produces a polymerized coating that is still easily removable with regular polish remover, that high percentage of acrylate and/or diacrylate monomer results in a finished coating that is very hard to remove. Therefore, while the percentages disclosed herein are also applicable to these monomers, they would be preferably reduced in embodiments based entirely on them. The exact degree by which the concentration of an acrylate used in substitution of a methacrylate (or a diacrylate used in substitution of a dimethacrylate) should be decreased depends on the desired properties of the final product and on the balance of the ingredients used in conjunction with the monomer. For example, a direct reduction to about 10 to 20 percent (that is, 10 to 20 parts of acrylate or diacrylate are used instead of 100 parts of methacrylate or dimethacrylate) of the amount listed in any formulation will yield acceptable results. In order to maintain the same percentages of the other ingredients, the balance may be made up with solvent. In general, though, I prefer to use acrylates and diacrylates, if at all, only in small quantities together with methacrylates and dimethacrylates because of their higher propensity to cause skin irritation.

Since acrylates and diacrylates are more reactive than methacrylates and dimethacrylates under the same conditions, higher amounts of inhibitors are required in order to prevent premature polymerization and ensure a useful shelf life. The proper, higher, percentage of inhibitor is found in the formulations in which the acrylate and diacrylate monomers are available commercially. For example, while a methacrylate is typically available in a solution containing 50 to 100 ppm of MEHQ, the homologous acrylate solution contains 100 to 200 ppm.

For the same reasons, as would be obvious to those skilled in the art, less photoinitiator is required to set off the polymerization reaction once the monomer is exposed to ultraviolet radiation. Typically, amounts smaller than those disclosed for methacrylates and dimethacrylates are found to work well with acrylates and diacrylates, respectively. It should be stressed, though, that these amounts are only guidelines for general formulations because different compositions with different percentages of inhibitors and photoinitiators will also work, but will exhibit obvious variations in shelf life and reactivity under UV light.

Most importantly, although acrylate and diacrylate monomers are adequate substitutes for methacrylates and dimethacrylates from the point of view of photoinitiated polymerization, I found them to be undesirable from a commercial point of view because of their higher toxicity. They tend to cause skin irritation, and sometime even blisters, in a large number of users. Therefore, I prefer compositions based entirely on methacrylate and dimethacrylate monomers, which were selected, in part, because they are known to be less toxic and generally less photoallergenic.

Thus, while the invention has been particularly shown and described with reference to a preferred embodiment thereof, it will be understood by those skilled in the art that changes in form and detail may be made therein without departing from the spirit and scope of the invention.

I claim:

1. A photo-reactive coating for application over and for binding with nail polish, comprising:

(a) a base resin consisting of nitrocellulose;

(b) a photo-reactive monomer selected from the group consisting of methacrylates, dimethacrylates, and mixtures thereof;

(c) a photoinitiator consisting of benzil diketal; and (d) an inhibitor to polymerization;

wherein said nitrocellulose is used in concentrations from 5 to 30 percent by weight of the total composition; wherein said photo-reactive monomer is used in concentrations from 2 to 55 percent by weight of the total composition; wherein said photoinitiator is used in concentrations from 0.05 to 5 percent by weight of the total composition; and wherein said inhibitor is used in concentrations from 25 to 200 parts per million.

2. The coating of claim 1, further comprising:

(e) an anti-oxidant;

wherein said anti-oxidant is used in concentrations between 0.10 and approximately 1.00 percent by weight of the total composition, said inhibitor is used in concentrations from to 200 parts per million, and the inhibitor is not an antioxidant.

3. The coating of claim 1, wherein said photo-reactive monomer is a dimethacrylate monomer of the following general formula:

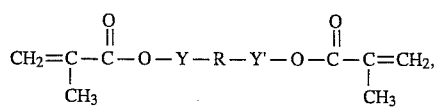

where Y and Y' may be the same or different but can be any hydrocarbyl difunctional radicals with 1–4 carbon atoms; R is any hydrocarbyl difunctional radical with 1–10 carbon atoms; the Y and Y' radicals may be joined to the R radical by means of any organic group with two free bonds, known to those skilled in the art as linking radicals, in which one or two atoms separate R from Y and Y'; and where R may be aliphatic, alicyclic or aromatic.

4. The coating of claim 1, wherein said photo-reactive monomer consists of at least one monomer from the class of methacrylic acid ester monomers.

5. The coating of claim 1, wherein said photo-reactive monomer consists of at least one monomer selected from the group consisting of 1,4 butanediol dimethacrylate, 1,3 butanediol dimethacrylate, diurethane dimethacrylate, ethyl methacrylate, 2-ethylhexyl methacrylate, cyclohexyl methacrylate, isobutyl methacrylate, n-butyl methacrylate, isobornyl methacrylate, furfuryl methacrylate, and tetrahydrofurfuryl methacrylate.

6. The coating of claim 1, wherein said photo-reactive monomer is ethyl methacrylate.

7. The coating of claim 1, wherein said photo-reactive monomer is cyclohexyl methacrylate.

8. The coating of claim 1, wherein said photo-reactive monomer is isobutyl methacrylate.

9. The coating of claim 1, wherein said photo-reactive monomer is methyl methacrylate.

10. The coating of claim 1, wherein said photo-reactive monomer is isobornyl methacrylate.

11. The coating of claim 1, wherein said photo-reactive monomer is furfuryl methacrylate.

12. The coating of claim 1, wherein said photo-reactive monomer is tetrahydro furfuryl methacrylate.

13. The coating of claim 3, wherein said dimethacrylate monomer is 1,4 butanediol dimethacrylate in concentrations from 0.5 to 5.5 percent by weight and wherein said coating further comprises a monofunctional methacrylate selected from the group consisting of ethyl methacrylate, cyclohexyl methacrylate, 2-ethylhexyl methacrylate, isobutyl methacrylate, n-butyl methacrylate, methyl methacrylate, isobornyl methacrylate, furfuryl methacrylate, tetrahydro furfuryl methacrylate, and mixtures thereof in concentrations from 2.0 to 55.0 percent by weight.

14. The coating of claim 3, wherein said dimethacrylate monomer is 1,3 butanediol dimethacrylate in concentrations from 0.5 to 5.5 percent by weight and wherein said coating further comprises a monofunctional methacrylate selected from the group consisting of ethyl methacrylate, cyclohexyl methacrylate, 2-ethylhexyl methacrylate, isobutyl methacrylate, n-butyl methacrylate, methyl methacrylate, isobornyl methacrylate, furfuryl methacrylate, tetrahydro furfuryl methacrylate, and mixtures thereof in concentrations from 2.0 to 55.0 percent by weight.

15. The coating of claim 3, wherein said dimethacrylate monomer is diurethane dimethacrylate in concentrations from 0.4 to 5.5 percent by weight and wherein said coating further comprises a monofunctional methacrylate selected from the group consisting of ethyl methacrylate, cyclohexyl methacrylate, 2-ethylhexyl methacrylate, isobutyl methacrylate, n-butyl methacrylate, methyl methacrylate, isobornyl methacrylate, furfuryl methacrylate, tetrahydro furfuryl methacrylate, and mixtures thereof in concentrations from 2.0 and 55.0 percent by weight.

16. The coating of claim wherein said inhibitor is hydroquinone.

17. The coating of claim wherein said inhibitor is 4-methoxyphenol hydroquinone.

18. A photo-reactive coating for application over and for binding with nail polish, comprising the following ingredients in the specified concentrations:

| Ingredient | Weight Percent |
| --- | --- |
| nitrocellulose | 22.9 |
| isopropyl alcohol | 9.8 |
| ethyl acetate | 32.75 |
| isobutyl acetate | 21.0 |
| n-butyl methacrylate | 7.14 |
| cyclohexyl methacrylate | 3.8 |
| tris(4-t-butyl-3-hydroxy-2, 6-dimethylbenzyl)-s-triazine-2, 4,6-trione | 0.42 |
| benzil diketal | 0.29 |
| 4-methoxyphenol | 11 ppm |
| dibutyl phthalate | 0.42 |
| sorbitan trioleate | 1.26 |
| fragrance | 0.21 |

19. A photo-reactive coating for application over and for binding with nail polish, comprising the following ingredients in the specified concentrations:

| Ingredient | Weight Percent |
| --- | --- |
| nitrocellulose | 17.2 |
| isopropyl alcohol | 7.4 |
| ethyl acetate | 32.5 |
| isobutyl acetate | 30.0 |
| cellulose acetate butyrate | 2.47 |
| butyl methacrylate resin | 0.91 |
| n-butyl methacrylate | 6.48 |
| cyclohexyl methacrylate | 2.14 |
| tris(4-t-butyl-3-hydroxy-2, 6-dimethylbenzyl)-s-triazine-2, 4,6-trione | 0.10 |
| benzil diketal | 0.28 |
| 4-methoxyphenol | 9 ppm |
| sorbitan trioleate | 0.54 |

20. A photo-reactive coating for application over and for binding with nail polish, comprising the following ingredients in the specified concentrations:

| Ingredient | Weight Percent |
| --- | --- |
| nitrocellulose | 9.3 |
| isopropyl alcohol | 4.0 |
| ethyl acetate | 53.2 |
| isobutyl acetate | 13.3 |
| butyl methacrylate resin | 0.73 |
| cellulose acetate propionate | 8.12 |
| n-butyl methacrylate | 6.65 |
| cyclohexyl methacrylate | 2.66 |
| tris(4-t-butyl-3-hydroxy-2, 6-dimethylbenzyl)-s-triazine-2, 4,6-trione | 0.27 |
| benzil diketal | 0.21 |
| 4-methoxyphenol | 9 ppm |
| dibutyl phthalate | 0.33 |
| sorbitan trioleate | 1.00 |
| fragrance | 0.22 |

21. A photo-reactive coating for nail polish for application over and for binding with said nail polish, comprising:

(a) a base resin consisting of nitrocellulose;

(b) a photo-reactive monomer selected from the group consisting of acrylates, diacrylates, methacrylates, dimethacrylates, and mixtures thereof;

(c) a photoinitiator; and (d) an inhibitor to polymerization; wherein said nitrocellulose is used in concentrations from 5 to 30 percent by weight of the total composition; said photoreactive monomer is used in concentrations from 2 to 55 percent by weight of the total composition, said acrylates and diacrylates being present in a cumulative amount not to exceed 11 percent by weight of the total composition; said photoinitiator is used in concentrations from 0.5 to 5 percent by weight of the total composition, and said inhibitor is used in concentrations from 100 to 200 parts per million.

\* \* \* \* \*

UNITED STATES PATENT AND TRADEMARK OFFICE
CERTIFICATE OF CORRECTION

PATENT NO. : 5,456,905
DATED : October 10, 1995
INVENTOR(S) : Vivian B. Valenty

It is certified that error appears in the above-indentified patent and that said Letters Patent is hereby corrected as shown below:

Column 14,
In Claim 2, line 18, insert: --6--after "concentrations from".

Signed and Sealed this

Twenty-sixth Day of December, 1995

Attest:

BRUCE LEHMAN

Attesting Officer     Commissioner of Patents and Trademarks